United States Patent

Timmler et al.

[11] 3,959,372
[45] May 25, 1976

[54] GLYOXYLIC ACID HYDRAZIDE-2-ACYLHYDRAZONE COMPOUNDS

[75] Inventors: Helmut Timmler; Wilfried Draber, both of Wuppertal, Germany

[73] Assignee: Bayer Aktiengesellschaft, Leverkusen, Germany

[22] Filed: Dec. 11, 1974

[21] Appl. No.: 531,637

[30] Foreign Application Priority Data
Dec. 24, 1973 Germany.............................. 2364474

[52] U.S. Cl............................ 260/561 H; 260/558 H
[51] Int. Cl.²..................................... C07C 103/32
[58] Field of Search..................... 260/558 H, 561 H

[56] References Cited
UNITED STATES PATENTS
3,886,211  5/1975  Keenan........................... 260/561 H
FOREIGN PATENTS OR APPLICATIONS
375,369  4/1964  Switzerland..................... 260/561 H Primary Examiner—C. Davis
Attorney, Agent, or Firm—Burgess, Dinklage & Sprung

[57] ABSTRACT

Novel glyoxylic acid hydrazide-2-acylhydrazones of the formula:

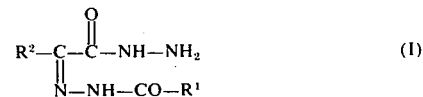

in which
R¹ is hydrogen or alkyl, and
R² is alkyl or optionally substituted phenyl and are prepared by reacting the corresponding glyoxylic acid ester 2-acylhydrazone with hydrazine hydrate. The compounds (I) are useful in preparing herbicidally active 4-amino-1,2,4-triazin-5-one compounds.

14 Claims, No Drawings

GLYOXYLIC ACID HYDRAZIDE-2-ACYLHYDRAZONE COMPOUNDS

The present invention relates to certain new glyoxylic acid hydrazide-2-acylhydrazone compounds.

The invention provides glyoxylic acid hydrazide-2-acylhydrazones of the general formula

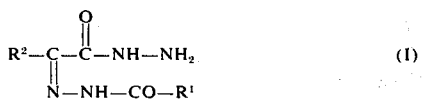

(I)

in which
R$^1$ is hydrogen or alkyl, and
R$^2$ is alkyl or optionally substituted phenyl.

When R$^1$ or R$^2$ is alkyl, it is preferably straight-chain or branched alkyl of from 1 to 6, especially 1 to 4, carbon atoms. Most preferably R$^1$ is methyl and R$^2$ is optionally substituted phenyl. Preferred possible substituents of the optionally monosubstituted or polysubstituted phenyl radical R$^2$ are straight-chain or branched alkyl of from 1 to 4 carbon atoms, alkoxy, alkylthio or alkylsulphonyl each of from 1 to 4 carbon atoms, halogen (especially fluorine, chlorine or bromine), haloalkyl or haloalkoxy each of from 2 to 5 halogen atoms and 1 or 2 carbon atoms (especially trifluoromethyl, pentafluoroethyl or trifluoromethoxy), and nitro, nitrile and/or thiocyanato.

The invention also provides a process for the production of a glyoxylic acid hydrazide-2-acylhydrazone of formula (I) in which a glyoxylic acid ester 2-acylhydrazone of the general formula

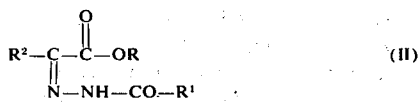

(II)

in which
R is alkyl of up to 4 carbon atoms, and
R$^1$ and R$^2$ have the meanings given above,
is reacted with hydrazine hydrate in the presence of a polar organic solvent at a temperature of 0° to 50°C.

A temperature of 0° to 30°C. is preferred.

1 to 1.5 mols of hydrazine hydrate are normally used per mol of the compound of formula (II).

The reaction is generally carried out under ambient pressure.

The compounds of the formula (I) may be isolated by cooling the reaction mixture to room temperature, filtering off the precipitate which has crystallized out, rinsing it with a little ethanol and drying it.

The glyoxylic acid ester 2-acylhydrazones of the formula (II) used as starting compounds are generally known and can be prepared according to customary methods as disclosed in German Offenlegungsschrift (German Published Specification) No. 2,107,757. The following may be mentioned individually as examples of the new glyoxylic acid hydrazide-2-acylhydrazones (I) which can be prepared from these by the process according to the invention: phenylglyoxylic acid hydrazide-2-acetylhydrazone, phenylglyoxylic acid hydrazide-2-propionylhydrazone, 4-fluorophenylglyoxylic acid hydrazide-2-propionylhydrazone, 3-methylphenylglyoxylic acid hydrazide-2-propionylhydrazone, 3-trifluoromethylphenylglyoxylic acid hydrazide-2-propionylhydrazone, 4-methoxyphenylglyoxylic acid hydrazide-2-propionylhydrazone, tertiary butylglyoxylic acid hydrazide-2-acetylhydrazone, 3-methoxyphenylglyoxylic acid hydrazide-2-acetylhydrazone, 3,4-dimethoxyphenylglyoxylic acid hydrazide-2-acetylhydrazone, 4-methylthiophenylglyoxylic acid hydrazide-2-acetylhydrazone, 4-methylsulphonylphenylglyoxylic acid hydrazide-2-propionylhydrazone, 4-chlorophenylglyoxylic acid hydrazide-2-propionylhydrazone and 4-trifluoromethoxyphenylglyoxylic acid hydrazide-2-propionylhydrazone.

Polar organic solvents can be used as diluents for the process according to the invention. Preferred ones include alcohols such as ethanol, n- and iso-propanol and n- and iso-butanol, acid amides such as dimethylformamide or hexamethylphosphoric acid triamide, and sulphoxides such as dimethylsulphoxide.

It is very surprising that the new glyoxylic acid hydrazide-2-acylhydrazones (I) of the invention are, on the one hand, stable compounds which can be isolated easily and, on the other hand, at elevated temperature undergo a smooth cyclization — by intramolecular reaction between the N-1 of the acid hydrazide group and the keto group, the activation of which is low, of the acylhydrazone group — with formation of 4-amino-1,2,4-triazin-5-ones which can even be "analytically pure".

The invention therefore also provides a process whereby a glyoxylic acid hydrazide-2-acylhydrazone of formula (I) is converted into a 4-amino-1,2,4-triazin-5-one of the general formula

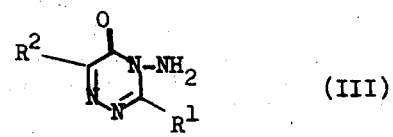

(III)

in which
R$^1$ and R$^2$ have the meanings given above, which comprises heating the compound of formula (I) in the presence of a polar organic solvent at a temperature of 60° to 150°C.

This heating is preferably carried out in the presence of a water-binding agent. Preferred agents include anhydrous powdered alkali metal carbonates, for example sodium carbonate, alkali metal sulphates, for example sodium sulphate, and alkali metal acetates, for example sodium acetate. However, the reaction can also be carried out without such an agent.

Polar organic solvents are also used as diluents for this heating step; the preferred ones are as described above.

The preferred heating temperature is 80° to 120°C. The heating is in general carried out under ambient pressure.

In carrying out the heating step, 1 to 1.2 mols of waterbinding agent are generally employed per mol of compound of formula (I).

The triazinones (III) may be isolated in substantially the same manner as the compounds of formula (I). A further fraction can in each case be obtained from the mother liquors by concentration. The triazinones (III) can be used direct as herbicides without further purification, since they can be obtained in a very pure form by the process according to the invention.

If phenylglyoxylic acid ethyl ester 2-acetylhydrazone is used as the starting material, the course of the two processes of the invention can be represented by the following formula schemes.

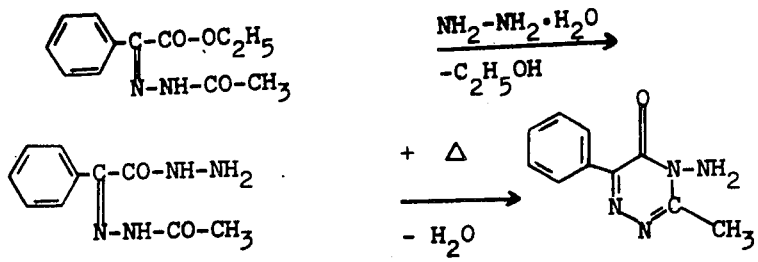

The 4-amino-1,2,4-triazin-5-ones (III) which can be prepared utilizing the inventive compounds are known as herbicides of good activity, as set forth in German Offenlegungsschriften (German Published Specifications) Nos. 2,107,757 and 2,138,031; furthermore, the use of those active compounds of the formula (III) herein wherein $R^1$ is methyl and $R^2$ is optionally substituted phenyl, as selective beet herbicides, forms the subject of an earlier patent application published as German Offenlegungsschrift (German Published Specification) No. 2,224,161.

It is already disclosed that 4-amino-1,2,4-triazin-5-ones are obtained when glyoxylic acid ester 2-acylhydrazones are reacted with hydrazine or hydrazine derivatives in the presence of a basic catalyst and of an organic solvent at 50° to 150°C, in accordance with the following formula scheme as disclosed in German Offenlegungsschrift (German Published Specification) No. 2,107,757:

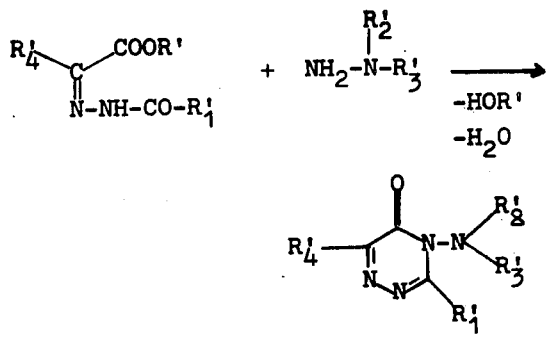

in which
$R_1'$ is alkyl or cycloalkyl,
$R_4'$ is $C(CH_3)_3$ or $C_6H_5$,
$R'$ is alkyl, and
$R_2'$ and $R_3'$ are hydrogen or alkyl.

However, the yields are not always satisfactory, especially when the process is carried out on an industrial scale.

Furthermore, it has been disclosed that 4-amino-1,2,4-triazin-5-ones can be obtained when diazabutadienes are reacted with hydrazine or alkylhydrazine in the presence of an acidbinding agent and in the presence of a diluent at 0° to 150°C. in accordance with the following formula scheme, in German Offenlegungsschrift (German Published Specification) No. 2,138,031:

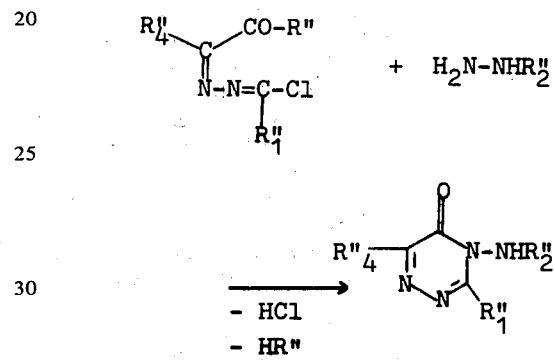

in which
R'' is chlorine or alkoxy,
$R_1''$ is alkyl or cycloalkyl,
$R_2''$ is alkyl or H, and
$R_4''$ is $C(CH_3)_3$ or $C_6H_5$.

This process, again, is not easy to carry out on an industrial scale. The diazabutadiene used as the starting material frequently still contains phosphorus oxychloride impurities and is therefore corrosive and of low stability. Furthermore, the purity of the triazinones produced is not always satisfactory so that the process has to be followed by additional purification processes.

Furthermore, it has been disclosed that 1,2,4-triazin-5-ones are obtained when amidrazones are reacted with α-keto-acid esters in the presence of an organic solvent at temperatures of −5° to 10°C. and thereafter heated to the boil in the presence of dimethylformamide, in accordance with the following formula scheme (collection Czechoslov. Chem. Commun. 36 (1971) 1955-1963):

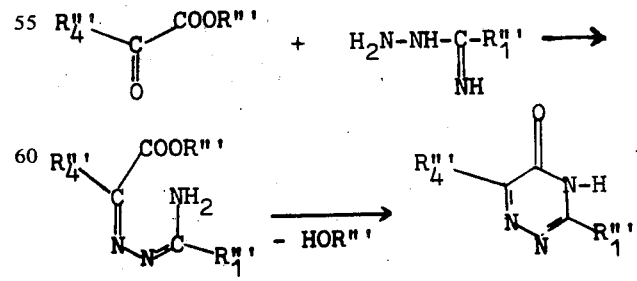

in which
$R_1'''$ is methyl or phenyl, and
$R_4'''$ is hydrogen or methyl (But 4-amino-1,2,4-triazin-5-ones cannot be prepared in this way).

The production of 4-amino-1,2,4-triazin-5-ones using the present invention has a number of technical advantages over these known methods. Thus, the glyoxylic acid ester 2-acylhydrazones (II) used as starting materials are easily accessible. The glyoxylic acid hydrazide-2-acylhydrazones (I) which function as intermediate products are also easily accessible by the process according to the invention and can be isolated relatively pure, as stable substances. The herbicidally active 4-amino-1,2,4-triazin-5-ones can be prepared in very good yields and excellent purity according to the invention. Effluent problems caused by solvents do not arise since the solvents can be recovered by distillation and are, furthermore, non-toxic.

The following examples illustrate the invention in more detail.

EXAMPLE 1A

Preparation on a Laboratory Scale of a Compound of General Formula (I)

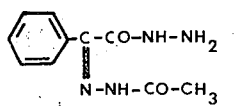

(I)-1

234 g (1 mol) of phenylglyoxylic acid ethyl ester 2-acetylhydrazones of melting point 88°C. were suspended in 1.5 liters of ethanol and 75 g (1 mol) of hydrazine hydrate were added over the course of 20 minutes at room temperature, while stirring. In the course thereof, the temperature rose to about 30°C. A clear, slightly yellowish-colored solution was produced, from which crystals began to separate out after a short time. After stirring for 4 hours at room temperature, the precipitate which had been produced, was filtered off, rinsed with a little ethanol and dried.

180 g (82% of theory) of phenylglyoxylic acid hydrazide-2-acetylhydrazone of melting point 177°C. were obtained.

EXAMPLE 1B

Preparation on a Laboratory Scale of a Compound of General Formula (III)

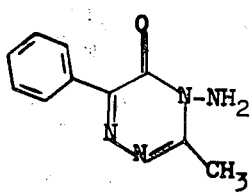

(III)-1

Variant (a)

175 g (0.8 mol) of phenylglyoxylic acid hydrazide-2-acetylhydrazone were dissolved in 2 liters of ethanol and the solution was heated to boil under reflux for 12 hours. After cooling, the product which had precipitated was filtered off. The mother liquor was partially freed from the solvent; on cooling, a further precipitate was obtained, which was also filtered off and well washed with water. The combined precipitates were dried. 123 g (76% of theory) of 4-amino-3-methyl-6-phenyl-1,2,4-triazin-5-(4H)-one of melting point 160°–163°C. were obtained.

Variant (b)

Variant (a) was repeated except that 66 g (0.8 mol) of anhydrous sodium acetate were added to the reactants specified. This increased the yield to 148 g (92% of theory); the melting point did not change.

EXAMPLE 1C

Preparation on an Industrial Scale of a Compound of General Formula (I)

262 kg (325 liters) of isopropanol and 84 kg (359 mols) of phenylglyoxylic acid ethyl ester 2-acetylhydrazone were initially introduced into a 500 liter stirred kettle. 27 kg (540 mols) of hydrazine hydrate were then added over the course of about 30 minutes at room temperature. Thereafter the mixture was stirred overnight at room temperature.

The resulting precipitate of phenylglyoxylic acid hydrazide-2-acetylhydrazone was filtered off and used in Example 1D in the moist state in which it was obtained from a centrifuge.

EXAMPLE 1D

Preparation on an Industrial Scale of a Compound of General Formula (III)

455 kg (570 liters) of n-propanol, 31.3 kg (381.7 mols) of sodium acetate and 84 kg of phenylglyoxylic acid hydrazide-2-acetylhydrazone, in the moist state in which it had obtained from a centrifuge (Example 1C), were initially introduced into a stirred kettle of 1,200 liters capacity. The kettle was brought to an internal temperature of 95°–100°C. and stirred for 20 hours at this temperature. After cooling to 5°–10°C., the resulting precipitate was filtered off, twice washed well with water and dried at 60°C.

The mother liquor was partially freed from the solvent, water was added to the viscous crystal sludge and the resulting precipitate was filtered off, well rinsed with water and dried.

50 kg (69% of theory, relative to phenylglyoxylic acid ethyl ester 2-acetylhydrazone) of 4-amino-3-methyl-6-phenyl-1,2,4-triazin-5-(4H)-one of melting point 160°–163°C. were obtained.

The compounds listed in Tables 1 (compounds of formula (I) and 2 (compounds of formula (III)), which follow, were prepared analogously to Example 1A - 1D.

Table 1

Compounds of formula (I):

$$R^2-\underset{N-NH-CO-R^1}{C}-\overset{O}{\underset{\|}{C}}-NH-NH_2 \quad (I)$$

| Example No. | $R^1$ | $R^2$ | Melting point (°C) |
|---|---|---|---|
| (I)-2 | $C_2H_5$ | phenyl | 149 |
| (I)-3 | $C_2H_5$ | F-phenyl | 173 |
| (I)-4 | $C_2H_5$ | $H_3CO$-phenyl | 159 |

Table 1-continued

Compounds of formula (I):

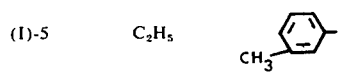

| Example No. | R¹ | R² | Melting point (°C) |
|---|---|---|---|
| (I)-5 | $C_2H_5$ | 4-CH₃-C₆H₄ | 140 |
| (I)-6 | $C_2H_5$ | 4-CF₃-C₆H₄ | 175 |
| (I)-7 | $CH_3$ | 4-F-C₆H₄ | 185 |
| (I)-8 | $CH_3$ | 3-F-C₆H₄ | 182 |

Table 2

Compounds of formula (III)

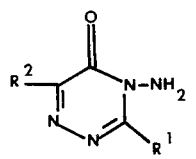

| Example No. | R¹ | R² | Melting point (°C) |
|---|---|---|---|
| (III)-2 | $C_2H_5$ | $C(CH_3)_3$ | 154 |
| (III)-3 | $C_2H_5$ | C₆H₅ | 164 |
| (III)-4 | $C_2H_5$ | 4-H₃C-C₆H₄ | 148 |
| (III)-5 | $C_2H_5$ | 4-CH₃O-C₆H₄ | 164–166 |
| (III)-6 | $C_2H_5$ | 3,4-(CH₃O)₂-C₆H₃ | 167–168 |
| (III)-7 | $C_2H_5$ | 4-Cl-C₆H₄ | 156 |
| (III)-8 | $C_2H_5$ | 3-CH₃-C₆H₄ | 108 |
| (III)-9 | $C_2H_5$ | 4-(CH₃)₃C-C₆H₄ | 133 |
| (III)-10 | $C_2H_5$ | 4-F-C₆H₄ | 149 |

Table 2-continued

Compounds of formula (III)

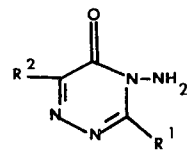

| Example No. | R¹ | R² | Melting point (°C) |
|---|---|---|---|
| (III)-11 | $C_2H_5$ | 4-CH₃O-C₆H₄ | 133 |
| (III)-12 | $C_2H_5$ | 4-Cl-C₆H₄ | 154 |
| (III)-13 | $C_2H_5$ | 4-CF₃-C₆H₄ | 132 |
| (III)-14 | $C_2H_5$ | 4-CF₃O-C₆H₄ | 159–160 |
| (III)-15 | $C_2H_5$ | 4-CH₃S-C₆H₄ | 178 |
| (III)-16 | $C_2H_5$ | 4-CH₃O₂S-C₆H₄ | 193–195 |
| (III)-17 | $C_2H_5$ | 4-O₂N-C₆H₄ | 180 |
| (III)-18 | $C_2H_5$ | 3-Cl-4-CF₃O-C₆H₃ | 126 |
| (III)-19 | H | $C(CH_3)_3$ | 113–114 |
| (III)-20 | $CH_3$ | 4-CH₃O-C₆H₄ | 206 |
| (III)-21 | $CH_3$ | $C(CH_3)_3$ | 158–159 |
| (III)-22 | $CH_3$ | C₆H₅ | 167–169 |
| (III)-23 | $CH_3$ | 4-H₃C-C₆H₄ | 199 |
| (III)-24 | $CH_3$ | 4-Cl-C₆H₄ | 97 |
| (III)-25 | $CH_3$ | 3-CH₃-C₆H₄ | 107 |
| (III)-26 | $CH_3$ | 4-(CH₃)₃C-C₆H₄ | 140 |
| (III)-27 | $CH_3$ | 3-CH₃-C₆H₄ | 178 |

Table 2-continued

Compounds of formula (III)

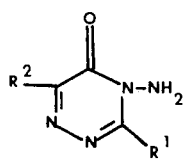

| Example No. | R¹ | R² | Melting point (°C) |
|---|---|---|---|
| (III)-28 | $CH_3$ | Cl-⌬- | 140 |
| (III)-30 | $CH_3$ | $CF_3$-⌬- | 169 |
| (III)-31 | $CH_3$ | $CF_3O$-⌬- | 189–191 |
| (III)-32 | $CH_3$ | $CH_3S$-⌬- | 209 |
| (III)-33 | $CH_3$ | $O_2N$-⌬- | 233 |
| (III)-34 | $CH_3$ | $CH_3O$-⌬-, $CH_3O$- | 220 |
| (III)-35 | $CH_3$ | $CF_3O$-⌬-, Cl- | 129 |
| (III)-36 | $CH_3$ | F-⌬- | 163 |
| (III)-37 | $CH_3$ | F-⌬- | 137 |

It will be understood that the foregoing specification and examples are illustrative but not limitative of the present invention inasmuch as other embodiments within the spirit and scope of the invention will suggest themselves to those skilled in the art.

What is claimed is:

1. Glyoxylic acid hydrazide-2-acylhydrazone compound of the formula:

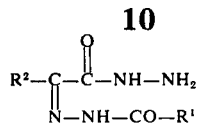

(I)

in which
R¹ is hydrogen or alkyl, and
R² is alkyl, phenyl, or substituted phenyl wherein the substituents are selected from alkyl, alkoxy, alkylthio, alkylsulfonyl, halogen, haloalkyl or haloalkoxy, nitro, nitrile and thiocyanato.

2. Glyoxylic acid hydrazide-2-acylhydrazone compound as claimed in claim 1 wherein R¹ is hydrogen.

3. Glyoxylic acid hydrazide-2-acylhydrazone compound as claimed in claim 1 wherein R¹ is alkyl of up to 6 carbon atoms.

4. Glyoxylic acid hydrazide-2-acylhydrazone compound as claimed in claim 1 wherein R² is alkyl.

5. Glyoxylic acid hydrazide-2-acylhydrazone compound as claimed in claim 1 wherein R² is phenyl.

6. Glyoxylic acid hydrazide-2-acylhydrazone compound as claimed in claim 1 wherein R² is mono-substituted phenyl.

7. Glyoxylic acid hydrazide-2-acylhydrazone compound as claimed in claim 1 wherein R² is poly-substituted phenyl.

8. Glyoxylic acid hydrazide-2-acylhydrazone compound as claimed in claim 1 wherein R² is phenyl substituted by at least one of $C_{1-4}$ alkyl, $C_{1-4}$ alkoxy, $C_{1-4}$ alkylthio, $C_{1-4}$ alkylsulfonyl, fluorine, chlorine, bromine, haloalkyl or haloalkoxy each with 2 to 5 halogen atoms and 1 or 2 carbon atoms, nitro, nitrile and thiocyanato.

9. Glyoxylic acid hydrazide-2-acylhydrazone compound as claimed in claim 1 designated phenylglyoxylic acid hydrazide-2-acetylhydrazone.

10. Glyoxylic acid hydrazide-2-acylhydrazone compound as claimed in claim 1 designated 3-methylphenylglyoxylic acid hydrazide-2-propionylhydrazone.

11. Glyoxylic acid hydrazide-2-acylhydrazone compound as claimed in claim 1 designated 4-fluorophenylglyoxylic acid hydrazide-2-acetylhydrazone.

12. Process for the preparation of a glyoxylic acid hydrazide-2-acylhydrazone compound as claimed in claim 1 which process comprises reacting a glyoxylic acid ester 2-acylhydrazone of the formula:

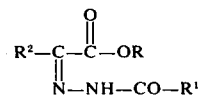

(II)

in which
R is alkyl of up to 4 carbon atoms, and
R¹ and R² are defined as in claim 1
with hydrazine hydrate in the presence of a polar organic solvent at a temperature of 0° to 50°C.

13. Process as claimed in claim 12 wherein the reaction temperature is from 0° to 30°C.

14. Process as claimed in claim 12 wherein 1 to 1.5 moles of hydrazine hydrate are employed per mole of the compound of formula (II).

* * * * *